United States Patent [19]

Davis

[11] Patent Number: 4,857,535

[45] Date of Patent: Aug. 15, 1989

[54] ANTI-SPASMODIC AGENTS HAVING A HETEROCYCLIC RING

[75] Inventor: William M. Davis, Tucson, Ariz.

[73] Assignee: United Pharmaceuticals, Tucson, Ariz.

[21] Appl. No.: 95,318

[22] Filed: Sep. 10, 1987

Related U.S. Application Data

[62] Division of Ser. No. 817,443, Jan. 9, 1986, Pat. No. 4,721,783.

[51] Int. Cl.$^4$ .................. A61K 31/40; A61K 31/495; A61K 31/535; A61K 31/54

[52] U.S. Cl. .................. 514/317; 514/227.5; 514/239.2; 514/239.5; 514/255; 514/256; 514/277; 514/299; 514/304; 514/305; 514/383; 514/400; 514/406; 514/428

[58] Field of Search ............... 514/222, 228, 255, 256, 514/277, 299, 304, 305, 317, 383, 400, 406, 428, 227.5, 239.2, 239.5

[56] References Cited

U.S. PATENT DOCUMENTS 2,390,555  12/1945  Richardson .................... 260/239
4,432,977   2/1984  Davis ........................... 424/248

OTHER PUBLICATIONS

Compte Rendue de la Societe de Biologie, 140, pp. 477–479, (1946), Dupre, Levy and Tchoubar.
Bulletin de la Societe Chimique, pp. 792–794, (1947), Tchoubar and Letellier–Dupre.
Farmakol i. Toskikol., pp. 10–17, (1956), Liberman with translation.
C. A. Buehler et al., Journal of Medicinal Chemistry 6, pp. 230–233, (1963).
C. A. Buehler et al., Journal of Medicinal Chemistry, vol. 8, p. 643, (Sep. 1965).
R. O. Clinto et al., Journal of the American Chemical Society, 68, pp. 2076–2077, (1946).
Goodman and Gilman, "The Pharmacological Basis of Therapeutics", 6th Ed., MacMillan Publishing Company, Inc., pp. 132 and 134.

*Primary Examiner*—Richard L. Raymond
*Attorney, Agent, or Firm*—Austin R. Miller

[57] ABSTRACT

A new method of treating a patient suffering from smooth muscle spasms involves treatment with a class of anti-spasmodic thioester compounds having a heterocyclic ring containing the nitrogen atom of a secondary or tertiary amine or a bicycloheterocyclic ring system containing the nitrogen atom of a secondary or tertiary amine. These compounds have the general formula I

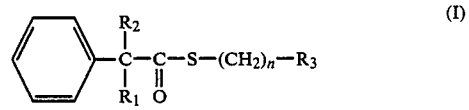

wherein:

n is an integer from 0 to 2;

$R_1$ is aryl or cycloalkyl;

$R_2$ is hydrogen or hydroxyl; and $R_3$ is selected from the group consisting of heterocyclic containing the nitrogen atom of a secondary or tertiary amine to which an alkyl group having from 0 to 3 carbon atoms is bonded and no other hetero atoms are present in the ring structure; heterocyclic containing the nitrogen atom of a secondary or tertiary amine to which an alkyl group having from 0 to 3 carbon atoms is bonded and one or more hetero atoms selected from the group consisting of N, O and S are present in the ring structure; bicycloheterocyclic ring system containing the nitrogen atom of a secondary or tertiary amine to which an alkyl group having from 0 to 3 carbon atoms is bonded and no other hetero atoms are present in the ring system; and bicycloheterocyclic ring system containing the nitrogen atom of a secondary or tertiary amine to which an alkyl group having from 0 to 3 carbon atoms is bonded and one or more hetero atoms selected from the group consisting of N, O and S are present in the ring system.

9 Claims, No Drawings

ANTI-SPASMODIC AGENTS HAVING A HETEROCYCLIC RING

This is a division of application Ser. No. 817,443, filed Jan. 9, 1986, now U.S. Pat. No. 4,721,783.

BACKGROUND OF THE INVENTION

1. Field of the Invention

The present invention relates to a method of treating patients for smooth muscle spasm with the use of new pharmaceutical compounds having useful anti-spasmodic properties.

2. Description of the Prior Art

The purpose of an anti-spasmodic drug is to relieve spasms of the smooth muscles. Smooth muscles line most of the visceral organs. The peristalsis and muscular activity of the stomach, intestines, gall bladder, urinary bladder, lung, the uterus, and to a degree the heart are all largely controlled by smooth muscles. Smooth muscles are innervated by the autonomic nervous system. The autonomic nervous system consists of two antagonistic branches—the sympathetic branch and the parasympathetic branch. On all visceral organs except the heart the parasympathetic nerve impulses increase the irritability and tension of the smooth muscles; contrariwise, the sympathetic nerve impulses increase the tension and irritability of the muscles of the heart muscle and relax the smooth muscles of the other visceral organs.

A spasm in a smooth muscle may be due to one of two causes. Either the smooth muscle may be receiving exaggerated impulses from the autonomic nervous system which create violent contractions in the muscle, or the muscle may be intrinsically stimulated into a spasm (most likely from chemical changes in the surrounding tissue). A spasm due to exaggerated impulses from the parasympathetic branch of the autonomic nervous system may often be corrected by administering atropine (an active alkaloid of belladonna, which serves to break a connection between the parasympathetic nerve and the smooth muscle. This ability and effect of atropine is called a "neurotropic effect". A spasm intrinsic in the smooth muscle itself may often be corrected by papaverine (a derivative of opium which is classed as a narcotic). Papaverine has an ability to decrease intrinsically the contractility of smooth muscle; it has the ability to relax smooth muscles directly. This ability and effect of papaverine is called a "musculotropic effect."

In relieving spasms of smooth muscles generally, a musculotropic effect is acknowledged to be superior to a neurotropic effect. A neurotropic effect cannot relieve spasms intrinsic in the smooth muscle itself, while a musculotropic effect, by relaxing and decreasing the irritability and responsiveness of smooth muscle to stimulation from the autonomic nervous system, can help to relieve a smooth muscle spasm even when it is due to exaggerated impulses from the autonomic nervous system.

Atropine produces undesirable side-reactions which presents a clinical difficulty. Atropine when given in effective doses, serves to break or partly break all the parasympathetic nerve-smooth muscle connections throughout the body. Thus when atropine is given in sufficient dosage to relieve a spasm in a specific visceral organ, such as a gastric or intestinal spasm (the spasm caused by exaggerated nerve impulses from the parasympathetic nervous system) undesirable side-actions due to the breaking of the parasympathetic nerve-muscle connections elsewhere in the body may occur. The most easily recognized of these undesirable side reactions are dilation of the pupil and dryness of the mouth, caused by the breaking of the parasympathetic connections to the iris and the saliva producing mechanism respectively.

Atropine is acknowledged to have also a musculotropic effect, but its neurotropic effect is so strong that atropine must be given in minute doses not exceeding (1/60 to 1/40 grain). A dosage of 1/6 to 1/40 of grain is too small to permit a significant musculotropic effect and when larger doses are administered undesirable side reactions are encountered.

U.S. Pat. No. 2,390,555 discloses a class of compounds comprising di-N-substituted aminoethyl esters of diphenylthioacetic acid of the general formula $(C_6H_5)_2$—CH—COS—$CH_2CH_2$—R in which R represents a disubstituted amino radical of either the diethylamino group, the morpholino group or the piperidino group with N as the point of attachment. This patent discloses that the thio analogs of certain disubstituted acetic acid esters of aminoalcohols have desirable anti-spasmodic properties. These compounds have proven to be very effective and are widely used as anti-spasmodics without encountering the undesirable side reactions due to excessive neurotropic effect.

U.S. Pat. No. 4,432,977 discloses new uses, especially for the dilation of the smooth muscles of the upper urinary tract, of the compounds disclosed in U.S. Pat. No. 2,390,555.

In *Compte Rendu de la Societe de Biologie*, 140, pp 477–9, (1946) Dupre, Levy and Tchoubar disclose a series of compounds having the formula $C_6H_5(R)CH$—$C(O)$—S—$CH_2CH_2N(CH_2CH_3)_2$ where R is either a phenyl group, a propyl group, an isopropyl group, a butyl group or an isoamyl group. These compounds are all disclosed as being spasmolytic agents.

Compounds of the same general formula given above are disclosed by Tchoubar and Letellier-Dupre in *Bulletin de la Societe Chimique*, pp 792–4 (1947) wherein R was a phenyl group, an ethyl group, a propyl group, an isopropyl group, a butyl group, an isoamyl group or hydrogen.

In *Farmakol. i. Toksikol.*, pp 10–17 (1956), Liberman discloses a class of compounds having the general formula $(C_6H_5)_2CHCOSCH_2CH_2N$—$R_2$, wherein both R's are the same and are selected from methyl, ethyl, propyl and butyl groups; and a class of compounds having the general formula $(C_6H_5)$—$CH(C_6H_{11})COSCH_2CH_2N$—$R_2$, wherein both R's are the same and are selected from methyl, ethyl, propyl and butyl groups.

C. A. Buehler et al. in the *Journal of Medicinal Chemistry*, 6, pp 230–3 (1963) disclose physiologically active compounds of the general formula $RR'C(OH)COS(CH_2)_xNR_2''\cdot HCl$ wherein R and R' are aryl groups, x is 2 or 3, and $R_2''$ is a methyl or ethyl group.

R. O. Clinton et al. in the *Journal of the American Chemical Society*, 68, pp 2076–7 (1946) disclose synthesis of a number of dialkyl aminoalkyl diarylthiolacetates including fluorene-9-carbothioic acid, S-[2-diethylaminoethyl]ester.

DESCRIPTION OF THE PREFERRED EMBODIMENTS

Patients suffering smooth muscle spasms are treated by administering effective amounts of a new class of anti-spasmodic compounds having the general formula I

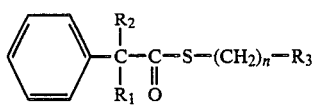

wherein:
n is an integer from 0 to 2;
$R_1$ is aryl or cycloalkyl;
$R_2$ is hydrogen or hydroxyl; and
$R_3$ is selected from the group consisting of heterocyclic containing the nitrogen atom of a secondary or tertiary amine to which an alkyl group having from 1 to 3 carbon atoms is bonded and no other hetero atoms are present in the ring structure; heterocyclic containing the nitrogen atom of a secondary or tertiary amine to which an alkyl group having from 0 to 3 carbon atoms is bonded and one or more hetero atoms selected from the group consisting of N, O and S are present in the ring structure; bicycloheterocyclic ring system containing the nitrogen atom of a secondary or tertiary amine to which an alkyl group having from 1 to 3 carbon atoms is bonded and no other hetero atoms are present in the ring system; and bicycloheterocyclic ring system containing the nitrogen atom of a secondary or tertiary amine to which an alkyl group having from 1 to 3 carbon atoms is bonded and one or more hetero atoms selected from the group consisting of N, O and S are present in the ring system.

The present invention also comprises methods of administering the above-described compounds for, but not limited to, the treatment of patients suffering from spasms in the upper and lower gastrointestinal tract, spasm associated with the gall bladder and common bile duct, as well as diarrhea, the irritable bowel syndrome, ureterospasm, bladder irritation, asthma, emphysema, and ophthalmologic injuries.

Representative heterocyclic rings include, but are not limited to, the following: 1-methyl-imidazolinyl, 1-ethyl-imidazolinyl, 1-n-propylimidazolinyl, 1-iso-propyl-imidazolinyl, 1-methyl-imidazolyl, 1-ethyl-imidazolyl, 1-n-propyl-imidazolyl, 1-iso-propylimidazolyl, 1-methyl-morpholinyl, 1-ethyl-morpholinyl, 1-n-propyl-morpholinyl, 1-iso-propyl-morpholinyl, 1-ethyl-piperazinyl, 1-n-propyl-piperazinyl, 1-iso-propyl-piperazinyl, 1-ethylpiperidinyl, 1-n-propyl-piperidinyl, 1-iso-propyl-piperidinyl, 1-methyl-pyrazolyl, 1-ethyl-pyrazolyl, 1-n-propyl-pyrazolyl, 1-iso-propyl-pyrazolyl, 1-n-propyl-pyrrolidinyl, 1-iso-propyl-pyrrolidinyl, 1-methyl-3-pyrrolinyl, 1-ethyl-3-pyrrolinyl, 1-n-propyl-3-pyrrolinyl, 1-iso-propyl-3-pyrrolinyl, 1-methyl-thiomorpholinyl, 1-ethyl-thiomorpholinyl, 1-n-propyl-thiomorpholinyl, 1-iso-propyl-thiomorpholinyl, 4-methyl-1,2,4-triazolyl, 4-ethyl-1,2,4-triazolyl, 4-n-propyl-1,2,4-triazolyl, 4-iso-propyl-1,2,4-triazolyl.

Representative compounds according to the method of this invention which contain bicycloheterocyclic ring systems include, but are not limited to, the following:

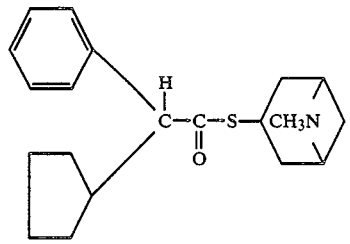

Cyclopentaneacetic acid, alpha-phenylthio, S-(3-alpha-tropanyl)ester

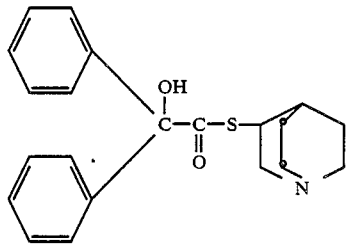

Benzilic acid, thio, S-(3-quinuclidinyl)ester

The general reaction in the synthesis of the anti-spasmodic compounds described in the following examples of the present invention involves the nucleophilic substitution of, for instance, diphenylacetyl chloride with certain heterocyclic thiol compounds. This reaction may be illustrated in the following scheme:

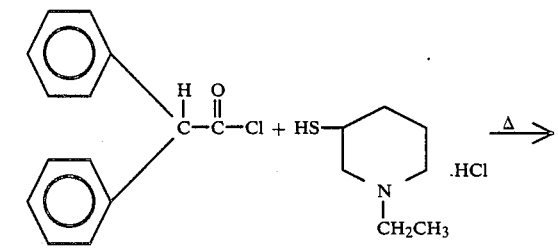

(diphenylacetyl chloride) (1-ethyl-3-mercapto-piperidine hydrochloride)

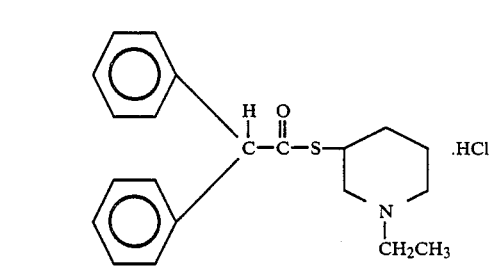

(3-diphenylthioacetyl-1-ethyl-piperidine hydrochloride)

The thiol containing a heterocyclic ring may be reacted with diphenylacetyl chloride in dichloromethane by combining the reactants in a 1:1 molar ratio and gently heating under reflux condensation for approximately 1-2 hours.

The desired acyl chlorides may be prepared from the carboxylic acid analogous by reaction with oxalyl chloride as follows:

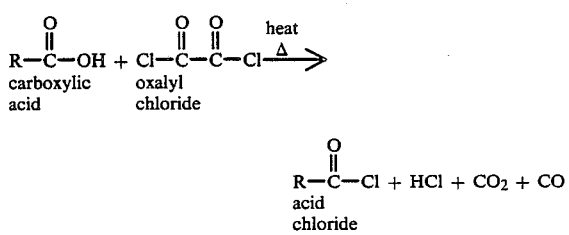

The reaction may be performed under reflux condensation. Following the reaction, which may be complete within a few hours, the acid chlorides may be vacuum-distilled and reacted with a thiol compound as described above.

The anti-spasmodic compounds used in the method of the present invention may be effective in a dosage range of from about 1 to about 15 mg/kilogram of body weight per day. A preferred dosage is in the range of from about 1.5 to about 11.5 mg/kilogram of body weight per day. A still more preferred dosage range is from about 3 to about 6 mg/kilogram of body weight per day.

The anti-spasmodic compounds used in the method of the present invention may be combined with a pharmaceutically acceptable carrier and may be administered orally, typically in tablets of 400 mg active ingredient, total 1155 mg, or by intravenous injection, or by topical application.

Because the anti-spasmodic compounds used in the method of the present invention may hydrolyze slowly in water, they are preferably not used as a solution or aqueous suspension unless freshly prepared compounds. It may be possible, however, to suspend the microspheres of these compounds in non-aqueous liquids for administration to patients.

As examples which are illustrative of, but are not limited to, the compounds used in the method of the present invention, there may be mentioned the following compounds designated as 1(a-x) through 10(a-x). $R_1$, $R_2$ and n for these compounds are located in Table I:

1(a-x)
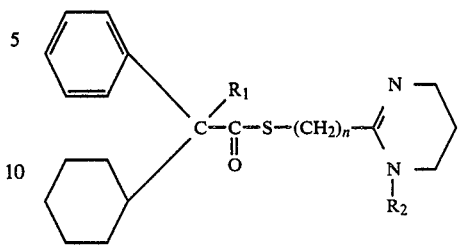

2(a-m) 2(o-x)
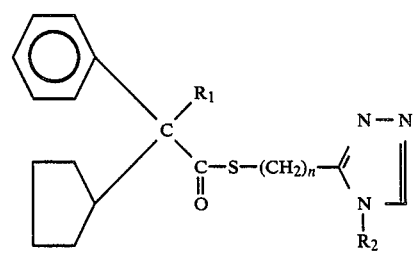

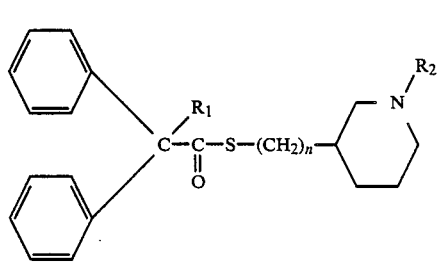

3(a-x)
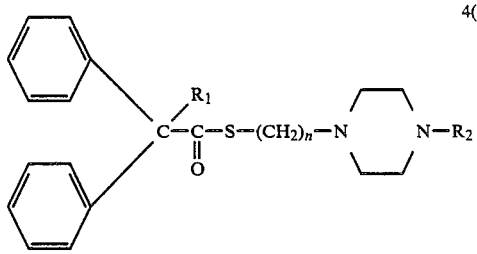

4(a-m) 4(o-x)
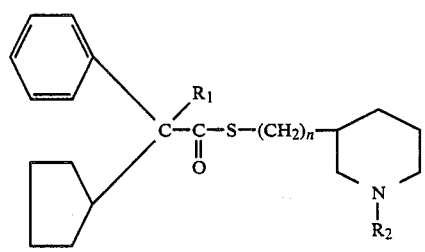

5(a-x)
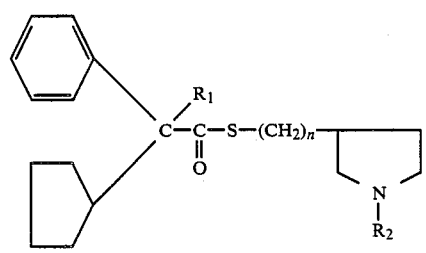

6(a-x)
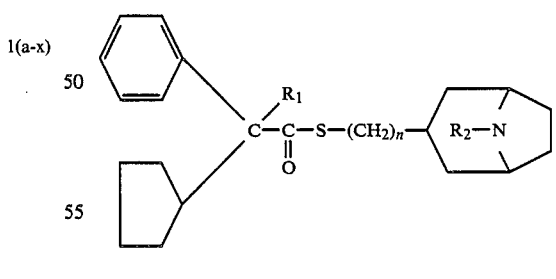

7(a-x)
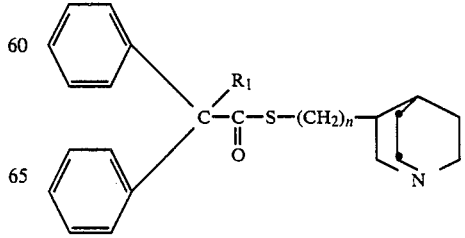

8(a-x)
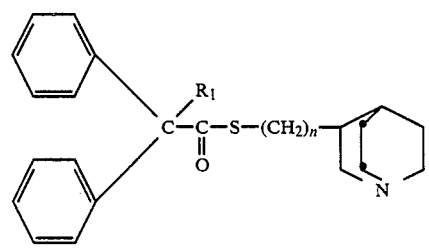

-continued

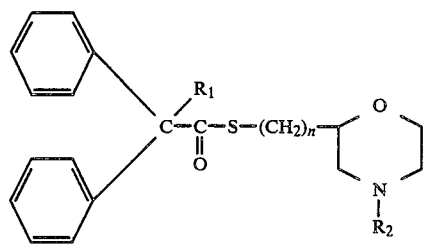
9(a-x)

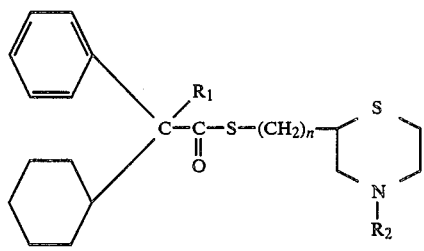
10(a-x)

TABLE I

|  | n | R₁ | R₂ |
| --- | --- | --- | --- |
| 1a-10a: | 0 | H | methyl |
| 1b-10b: | 0 | H | ethyl |
| 1c-10c: | 0 | H | n-propyl |
| 1d-10d: | 0 | H | iso-propyl |
| 1e-10e: | 1 | H | methyl |
| 1f-10f: | 1 | H | ethyl |
| 1g-10g: | 1 | H | n-propyl |
| 1h-10h | 1 | H | iso-propyl |
| 1i-10i: | 2 | H | methyl |
| 1j-10j: | 2 | H | ethyl |
| 1k-10k: | 2 | H | n-propyl |
| 1l-10l: | 2 | H | iso-propyl |
| 1m-10m: | 0 | OH | methyl |
| 1n-10n: | 0 | OH | ethyl |
| 1o-10o: | 0 | OH | n-propyl |
| 1p-10p: | 0 | OH | iso-propyl |
| 1q-10q: | 1 | OH | methyl |
| 1r-10r: | 1 | OH | ethyl |
| 1s-10s: | 1 | OH | n-propyl |
| 1t-10t: | 1 | OH | iso-propyl |
| 1u-10u: | 2 | OH | methyl |
| 1v-10v: | 2 | OH | ethyl |
| 1w-10w: | 2 | OH | n-propyl |
| 1x-10x: | 2 | OH | iso-propyl |

The compounds used in the method of this invention are anti-muscarinic agents (cholinergic-muscarinic receptor antagonists) which inhibit the actions of acetylcholine on autonomic effectors innervated by postganglionic cholinergic nerves as well as on smooth muscle that lacks cholinergic innervation. Since a major component of parasympathetic control of smooth muscle occurs via muscarinic receptors, these compounds may be effective as modifiers of smooth muscle activity.

Thiphenamil hydrochloride has been shown to decrease spasms of the gastrointestinal tract, biliary tract, ureter and uterus without producing characteristic atropinic side effects on salivary and sweat glands, GI glands, or the cardiovascular system. This invention results in the use of compounds which may be as efficacious as thiphenamil hydrochloride, or more so, in relaxing various smooth muscle systems while at the same time demonstrating thiphenamil hydrochloride's lack of associated side-effects.

I claim:

1. A method of treating a patient suffering smooth muscle spasm comprising administering to the patient an effective amount of an anti-spasmodic agent comprising a compound of formula I

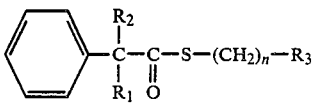
(I)

wherein:
n is an integer from 0 to 2;
R₁ is aryl or cycloalkyl;
R₂ is hydrogen or hydroxyl; and
R₃ is a heterocyclic or bicycloheterocyclic nitrogen ring connected to the main chain and is selected from the group consisting of heterocyclic containing the nitrogen atom of a secondary or tertiary amine to which an alkyl group having 1 to 3 carbon atoms is bonded and no other hetero atoms are present in the ring structure; heterocyclic containing the nitrogen atom of a secondary or tertiary amine to which an alkyl group having from 1 to 3 carbon atoms is bonded and one or more hetero atoms selected from the group consisting of N, O and S are present in the ring structure; bicycloheterocyclic ring system containing the nitrogen atom of a secondary or tertiary amine to which an alkyl group having 1 to 3 carbon atoms is bonded and no other hetero atoms are present in the ring system; and bicycloheterocyclic ring system containing the nitrogen atom of a secondary or tertiary amine to which an alkyl group having from 1 to 3 carbon atoms is bonded and one or more hetero atoms selected from the group consisting of N, O and S are present in the ring system.

2. The method as defined in claim 1, wherein the compound is administered in a dosage of from about 1 to about 15 mg/kg of body weight per day.

3. The method as defined in claim 1, wherein the compound is administered in a preferred dosage from about 1.5 to about 11.5 mg/kg of body weight per day.

4. The method as defined in claim 1, wherein the compound is administered in a more preferred dosage of from about 3 to about 6 mg/kg of body weight per day.

5. The method as defined in claim 1, wherein the compound is combined with a pharmaceutically acceptable carrier.

6. A method of treating a patient suffering from smooth muscle spasm comprising the step of administering an effective amount of an antispasmodic agent having the formula

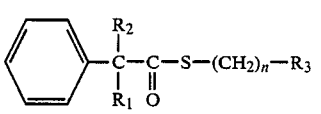
(I)

wherein:
n is an integer from 0 to 2;
R₁ is aryl or cycloalkyl;
R₂ is hydrogen or hydroxyl; and
R₃ is a heterocyclic nitrogen ring connected to the main chain and is selected from the group consisting of 1-methylimidazolinyl, 1-ethyl-imidazolinyl, 1-n-propyl-imidazolinyl, 1-iso-propyl-imidazolinyl, 1-methyl-imidazolyl, 1-ethyl-imidazolyl, 1-n-propyl-imidazolyl, 1-iso-propyl-imidazolyl, 1-methylmorpholinyl, 1-ethyl-morpholinyl, 1-n-propyl-morpholinyl, 1-iso-propyl-morpholinyl, 1-ethyl-piperazinyl, 1-n-propyl-piperazinyl, 1-iso-propyl-piperazinyl, 1-n-propyl-piperidinyl, 1-iso-propyl-piperidinyl, 1-methyl-pyrazolyl, 1-ethyl-pyrazolyl, 1-n-propylpyrazolyl, 1-iso-propyl-pyrazolyl, 1-n-propyl-pyrrolidinyl, 1-iso-propyl-pyrrolidinyl, 1-methyl-3-pyrrolinyl, 1-ethyl-3-pyrrolidinyl, 1-n-propyl-3-pyrrolidinyl, 1-iso-propyl-3-pyrrolinyl, 1-methyl-thiomorpholinyl, 1-ethyl-thiomorpholinyl, 1-n-propyl-thiomorpholinyl, 1-iso-propyl-thiomorpholinyl, 4-methyl, 1,2,4-triazolyl, 4-ethyl-1,2,4-triazolyl, 4-n-propyl-1,2,4-triazolyl, 4-iso-propyl-1,2,4-triazolyl.

7. A method of treating a patient suffering smooth muscle spasm comprising administering to the patient an effective amount of an anti-spasmodic agent comprising a compound having a formula selected from the group consisting of

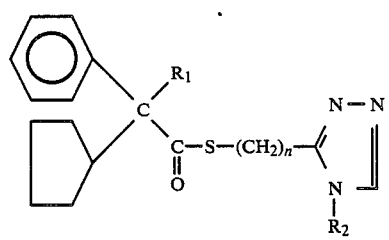

1(a-x)

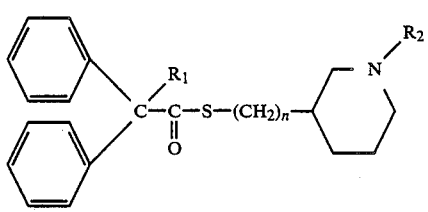

2(a-x)

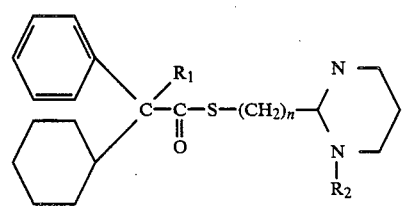

3(a-x)

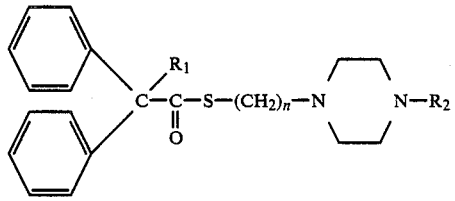

4(a-x)

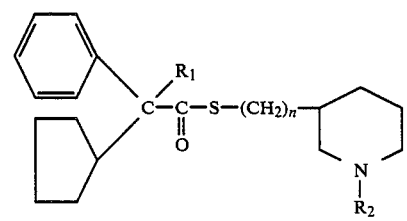

5(a-x)

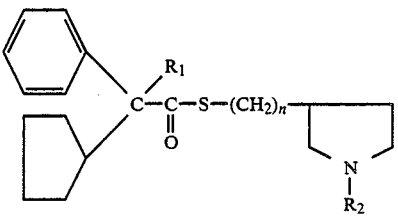

6(a-x)

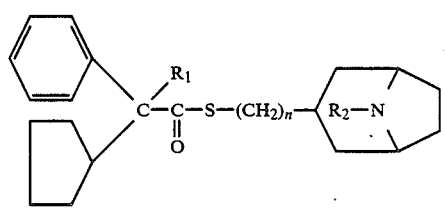

7(a-x)

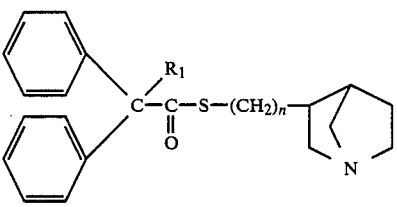

8(a-x)

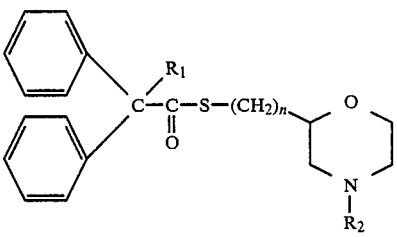

9(a-x)

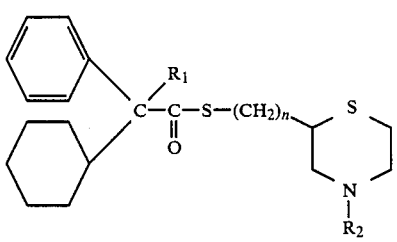

10(a-x)

where n is an integer from 0 to 2, $R_1$ is H or OH and $R_2$ is selected from the group consisting of methyl, ethyl, n-propyl and isopropyl, and where (a) through (x) are combinations of n, $R_1$ and $R_2$ as defined in Table 1.

8. A method of treating a patient suffering smooth muscle spasm comprising administering to the patient an effective amount of an anti-spasmodic agent comprising a compound having a formula selected from the group consisting of

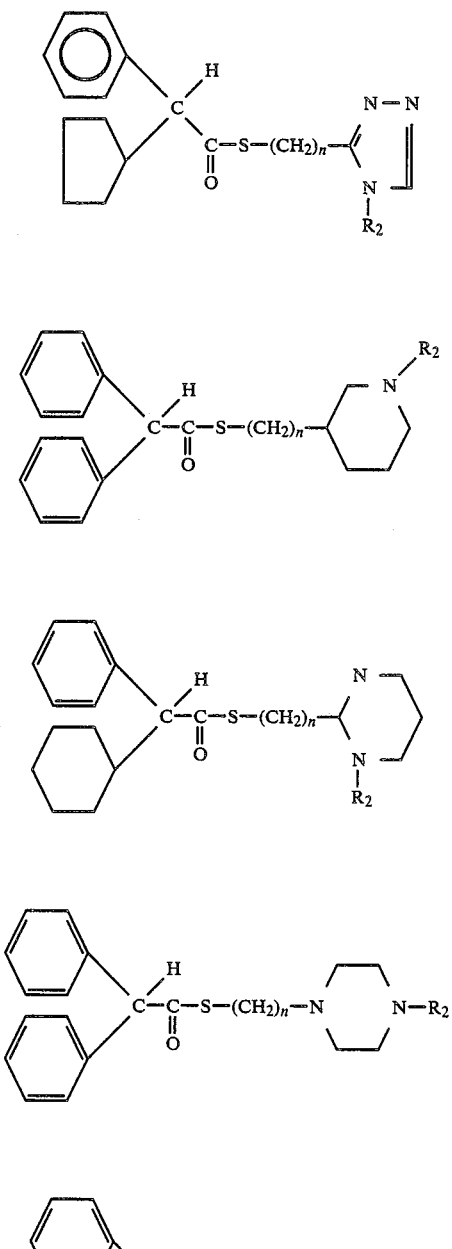

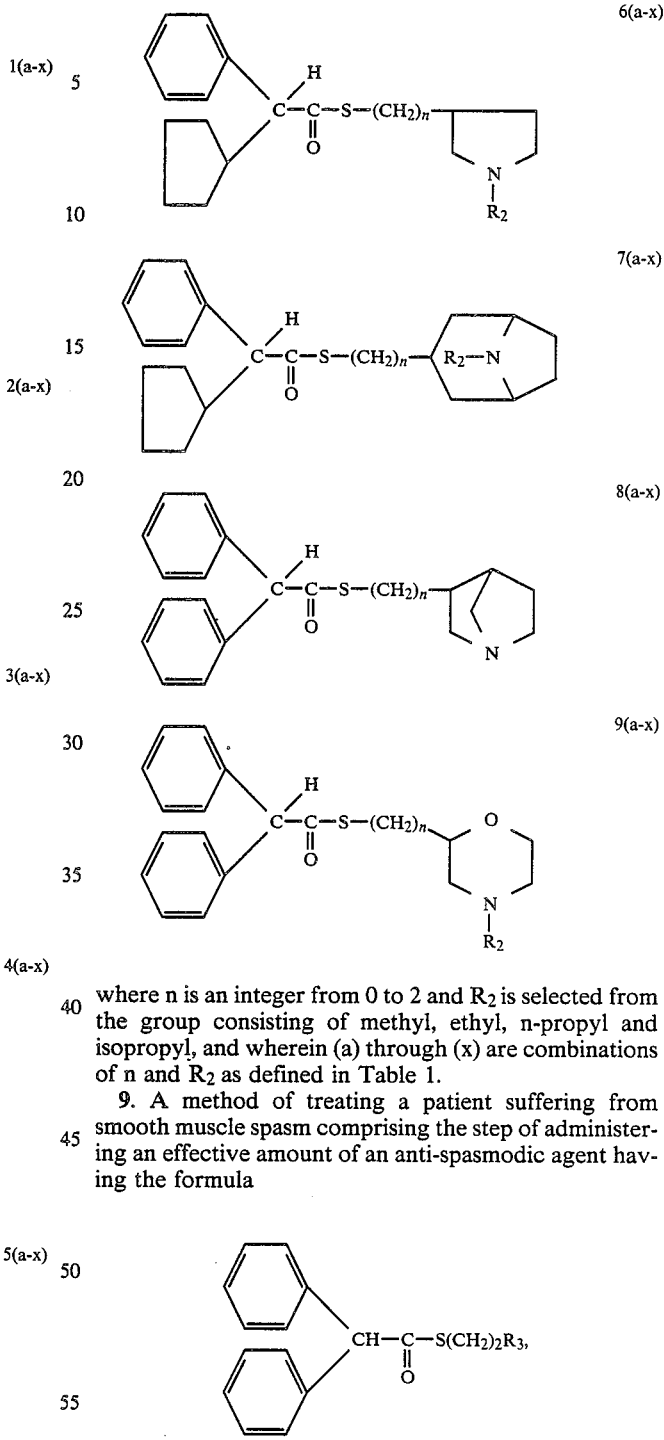

where n is an integer from 0 to 2 and $R_2$ is selected from the group consisting of methyl, ethyl, n-propyl and isopropyl, and wherein (a) through (x) are combinations of n and $R_2$ as defined in Table 1.

9. A method of treating a patient suffering from smooth muscle spasm comprising the step of administering an effective amount of an anti-spasmodic agent having the formula

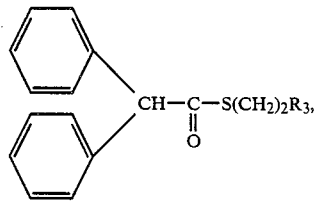

where $R_3$ is 1-ethyl-piperidinyl.

* * * * *